(12) United States Patent
Takenaka et al.

(10) Patent No.: US 10,961,514 B2
(45) Date of Patent: Mar. 30, 2021

(54) FLAVIN-CONJUGATED GLUCOSE DEHYDROGENASE

(71) Applicant: IKEDA FOOD RESEARCH CO., LTD., Hiroshima (JP)

(72) Inventors: Ryo Takenaka, Hiroshima (JP); Takafumi Takumi, Hiroshima (JP)

(73) Assignee: IKEDA FOOD RESEARCH CO., LTD., Hiroshima (JP)

(*) Notice: Subject to any disclaimer, the term of this patent is extended or adjusted under 35 U.S.C. 154(b) by 143 days.

(21) Appl. No.: 16/069,239

(22) PCT Filed: Jan. 11, 2017

(86) PCT No.: PCT/JP2017/000546
§ 371 (c)(1),
(2) Date: Sep. 28, 2018

(87) PCT Pub. No.: WO2017/122650
PCT Pub. Date: Jul. 20, 2017

(65) Prior Publication Data
US 2019/0024057 A1    Jan. 24, 2019

(30) Foreign Application Priority Data

Jan. 14, 2016 (JP) .............................. JP2016-004950

(51) Int. Cl.
| C12N 9/04 | (2006.01) |
| C12M 1/40 | (2006.01) |
| C12Q 1/32 | (2006.01) |
| C12Q 1/54 | (2006.01) |

(52) U.S. Cl.
CPC ............. *C12N 9/0006* (2013.01); *C12M 1/40* (2013.01); *C12Q 1/32* (2013.01); *C12Q 1/54* (2013.01); *C12Y 101/9901* (2013.01)

(58) Field of Classification Search
CPC .......... C12N 9/0006; C12Q 1/32; C12Q 1/54; C12Y 101/9901; C12M 1/40
See application file for complete search history.

(56) References Cited

U.S. PATENT DOCUMENTS

| 7,514,250 | B2 | 4/2009 | Omura et al. |
| 8,492,130 | B2 | 7/2013 | Yada et al. |
| 8,691,547 | B2 | 4/2014 | Omura et al. |
| 8,945,359 | B2 | 2/2015 | Honda et al. |
| 9,506,042 | B2 | 11/2016 | Sumida et al. |
| 2005/0191627 | A1 | 9/2005 | Yang et al. |
| 2006/0063217 | A1 | 3/2006 | Omura et al. |
| 2007/0042377 | A1 | 2/2007 | Gao et al. |
| 2008/0014612 | A1 | 1/2008 | Tsuji et al. |
| 2008/0020426 | A1 | 1/2008 | Aiba et al. |
| 2009/0155848 | A1 | 6/2009 | Aiba et al. |
| 2009/0181408 | A1 | 7/2009 | Tanaka et al. |
| 2009/0259024 | A1 | 10/2009 | Tsuji et al. |
| 2011/0033880 | A1 | 2/2011 | Yada et al. |
| 2011/0318810 | A1 | 12/2011 | Tajima et al. |
| 2012/0122130 | A1 | 5/2012 | Omura et al. |
| 2012/0171708 | A1 | 7/2012 | Kawaminami et al. |
| 2013/0122149 | A1 | 5/2013 | Toscano et al. |
| 2013/0203093 | A1 | 8/2013 | Honda et al. |
| 2014/0154777 | A1 | 6/2014 | Sumida et al. |
| 2014/0287478 | A1 | 9/2014 | Sumida et al. |
| 2014/0302542 | A1 | 10/2014 | Araki |
| 2015/0031059 | A1 | 1/2015 | Sumida et al. |
| 2015/0111280 | A1* | 4/2015 | Sumida ................. C12Q 1/32 435/190 |
| 2015/0152394 | A1 | 6/2015 | Honda et al. |
| 2015/0240216 | A1 | 8/2015 | Yamazaki et al. |
| 2015/0267178 | A1 | 9/2015 | Ozawa et al. |
| 2017/0088823 | A1 | 3/2017 | Takumi et al. |

FOREIGN PATENT DOCUMENTS

| JP | 2007-289148 | 11/2007 |
| JP | 2010-57427 | 3/2010 |
| JP | 2011-97931 | 5/2011 |
| JP | 2011-103792 | 6/2011 |
| JP | 2011-115156 | 6/2011 |

(Continued)

OTHER PUBLICATIONS

UniProt Accession No. L2G906, Glucose oxidase (Created Mar. 6, 2013).*
Sierks et al. Active Site Similarities of Glucose Dehydrogenase, Glucose Oxidase, and Glucoamylase Probed by Deoxygenated Substrates. Biochemistry, 1992, 31: 8972-8977.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36): 11643-50.*

(Continued)

*Primary Examiner* — Iqbal H Chowdhury
(74) *Attorney, Agent, or Firm* — Wenderoth, Lind & Ponack, L.L.P.

(57) ABSTRACT

The present invention relates to a protein having glucose dehydrogenase activity selected from: (a) an amino acid sequence represented by SEQ ID NO: 3; (b) an amino acid sequence in which 1 to 3 amino acids are deleted from, replaced in or added to the amino acid sequence represented by SEQ ID NO: 3; (c) an amino acid sequence which has at least 80% identity with the amino acid sequence represented by SEQ ID NO: 3 and whose N-terminus is SS; or (d) an amino acid sequence which has at least 80% identity with the amino acid sequence represented by SEQ ID NO: 3, and does not contain a sequence represented by SEQ ID NO: 8 at its N-terminus. The invention also includes a polynucleotide encoding the enzyme, a method for manufacturing the enzyme, a method for measuring glucose using the enzyme, a measuring reagent composition and a biosensor.

7 Claims, 2 Drawing Sheets
Specification includes a Sequence Listing.

(56) References Cited

FOREIGN PATENT DOCUMENTS

| | | |
|---|---|---|
| JP | 2011-152129 | 8/2011 |
| JP | 2011-217731 | 11/2011 |
| JP | 2011-217755 | 11/2011 |
| JP | 2013-90620 | 5/2013 |
| WO | 2004/058958 | 7/2004 |
| WO | 2006/101239 | 9/2006 |
| WO | 2007/116710 | 10/2007 |
| WO | 2007/139013 | 12/2007 |
| WO | 2008/001903 | 1/2008 |
| WO | 2009/087929 | 7/2009 |
| WO | 2010/140431 | 12/2010 |
| WO | 2011/034108 | 3/2011 |
| WO | 2013/031664 | 3/2013 |
| WO | 2013/051704 | 4/2013 |
| WO | 2013/065770 | 5/2013 |
| WO | 2013/147206 | 10/2013 |
| WO | 2014/002973 | 1/2014 |
| WO | 2014/045912 | 3/2014 |

OTHER PUBLICATIONS

Auclair et al. Review, Signal peptidase I: Cleaving the way to mature proteins. Protein Science (2012), 21:13-25.*
Gan et al. Comparative genomic and transcriptomic analyses reveal the hemibiotrophic stage shift of Colletotrichum fungi. New Phytologist (2013), 197:1236-1249.*
International Search Report dated May 14, 2013 in International (PCT) Application No. PCT/JP2013/059639, with English translation.
International Search Report dated May 12, 2015 in International Application No. PCT/JP2015/058171.
Database GenBank [online] Accession No. CDM29258, Feb. 4, 2014 uploaded, [retrieved on Apr. 20, 2015], Definition: Glucose-methanol-choline oxidoreductase [Penicillium roqueforti], http://www.ncbi.nlm.nih.gov/protein/584417546? sat=18&satkey=3685927.
Cavener, D.R., "GMC oxidoreductases. A Newly Defined Family of Homologous Proteins with Diverse Catalytic Activities", J. Mol. Biol., 1992, vol. 223, No. 3, pp. 811-814.
Mori, K. et al., "Screening of *Aspergillus*-derived FAD-glucose dehydrogenases from fungal genome database", Biotechnol. Lett., 2011, vol. 33, pp. 2255-2263.
Sygmund et al., "Heterologous overexpression of Glomerella cingulata FAD-dependent glucose dehydrogenase in *Escherichia coli* and *Pichi pastoris*", Microbial Cell Factories, 2011, 10(1): 106.
Witkowski et al., "Conversion of a β-Ketoacyl Synthase to a Malonyl Decarboxylase by Replacement of the Active-Site Cysteine with Glutamine", Biochemistry 38: 11643-11650, 1999.
Seffernick et al., "Melamine Deaminase and Atrazine Chlorohydrolase: 98 Percent Identical but Functionally Different" J. Bacteriol. 183(8):2405-2410, 2001.
Brandon et al., "Introduction to Protein Structure", Garland Publishing Inc., New York, pp. 247, 1991.
Sadowski et al., "The sequence-structure relationship and protein function prediction", Current Opinion in Structural Biology 19: 357-362, 2009.
Anastassiadis et al., "Continuous gluconic acid production by isolated yeast-like mould strains of *Aureobasidium pullulans*", Appl. Microbiol Biotechnol (2003), 61: 110-17.
Bankar et al., "Glucose oxidase—An overview", Biotechnology Advances, 27 (2009) 489-501.
Frederick et al., "Glucose Oxidase from *Aspergillus niger*", The Journal of Biological Chemistry, vol. 265, No. 7, Mar. 5, 1990, pp. 3793-3802.
Uniprot, Accession No. A0A074X3M2, 2016, www.uniprot.org.
International Search Report dated Apr. 4, 2017 in International Application No. PCT/JP2017/000546.
Christoph Sygmund et al., "Reduction of quinones and phenoxy radicals by extracellular glucose dehydrogenase from *Glomerella cingulata* suggests a role in plant pathogenicity", Microbiology (2011), 157, 3203-3212.
GenBank: ELA35154.1, "glucose oxidase [Collectotrichum gloeosporioides Nara gc5]", known sequence having 98.5% identity to SEQ ID No. 3 of the present invention.

* cited by examiner

FLAVIN-CONJUGATED GLUCOSE DEHYDROGENASE

TECHNICAL FIELD

The present invention relates to a glucose dehydrogenase, a polynucleotide encoding the enzyme, a method for manufacturing the enzyme, a method for measuring glucose using the enzyme, a measuring reagent composition, a biosensor and the like.

BACKGROUND ART

Measurement of a blood glucose (blood sugar) concentration is important primarily in blood sugar control for a diabetes patient. For measuring blood sugar, biosensors are widely used as blood sugar meters utilizing enzymes.

As enzymes usable for biosensors, glucose oxidases and glucose dehydrogenases are known. However, the glucose oxidases had problems that measurement errors are caused by dissolved oxygen in the blood. Among the glucose dehydrogenases, flavin-conjugated glucose dehydrogenases derived from eukaryotic cells are not affected by dissolved oxygen, require no addition of coenzymes, and have an excellent substrate specificity, and thus they are useful as enzymes for biosensors (Patent Documents 1 to 5).

PRIOR ART DOCUMENTS

Patent Documents

Patent Document 1: International Publication No. WO 2004/058958
Patent Document 2: International Publication No. WO 2006/101239
Patent Document 3: International Publication No. WO 2008/001903
Patent Document 4: International Publication No. WO 2013/031664
Patent Document 5: International Publication No. WO 2013/147206

SUMMARY OF INVENTION

Problem to be Solved

In blood sugar measurement, an enzyme with higher substrate specificity has been desired. The present invention provides a glucose dehydrogenase with high substrate specificity, a polynucleotide encoding the enzyme, a method for manufacturing the enzyme, a method for measuring glucose using the enzyme, a measuring reagent composition and a biosensor. Furthermore, the present invention provides methods for manufacturing the measuring reagent composition and the biosensor.

Solution to Problem

The inventors searched for various microorganism-derived glucose dehydrogenases, and then found a flavin-conjugated glucose dehydrogenase with high substrate specificity. Furthermore, the inventors found an efficient method for manufacturing the flavin-conjugated glucose dehydrogenase to complete the present invention.

That is, the present invention relates to the following aspects [1] to [8].

[1] A protein having the following amino acid sequence (a), (b), (c) or (d), and having glucose dehydrogenase activity:
(a) an amino acid sequence represented by SEQ ID NO: 3;
(b) an amino acid sequence in which 1 to 3 amino acids are deleted from, replaced in or added to the amino acid sequence represented by SEQ ID NO: 3;
(c) an amino acid sequence which has at least 80% identity with the amino acid sequence represented by SEQ ID NO: 3 and whose N-terminus is SS
(d) an amino acid sequence which has at least 80% identity with the amino acid sequence represented by SEQ ID NO: 3, and does not contain a sequence represented by SEQ ID NO: 8 at its N-terminus.
[2] The protein according to [1] which does not use oxygen as an electron acceptor.
[3] The protein according to [1] or [2] which is a recombinant protein obtained by making a vector containing a polynucleotide encoding glucose dehydrogenase, and culturing a transformant cell which was transformed by the vector.
[4] A polynucleotide encoding the protein according to [1].
[5] A recombinant vector containing the polynucleotide according to [4].
[6] A transformant cell which was transformed by the vector according to [5].
[7] A method for manufacturing a flavin-conjugated glucose dehydrogenase, characterized in that the cell according to [6] is cultured, and the flavin-conjugated glucose dehydrogenase is collected from the culture.
[8] A method for measuring glucose not substantially affected by dissolved oxygen, using the flavin-conjugated glucose dehydrogenase which is composed of a protein having the following amino acid sequence (a), (b), (c), (d) or (e) and glucose dehydrogenase activity, and which does not use oxygen as an electron acceptor:
(a) an amino acid sequence represented by SEQ ID NO: 3;
(b) an amino acid sequence in which 1 to 3 amino acids are deleted from, replaced in or added to the amino acid sequence represented by SEQ ID NO: 3;
(c) an amino acid sequence which has at least 80% identity with the amino acid sequence represented by SEQ ID NO: 3 and whose N-terminus is SS;
(d) an amino acid sequence which has at least 80% identity with the amino acid sequence represented by SEQ ID NO: 3, and does not contain a sequence represented by SEQ ID NO: 8 at its N-terminus;
(e) an amino acid sequence having at least 80% identity with the amino acid sequence represented by SEQ ID NO: 3.
[9] A glucose measuring reagent composition not substantially affected by dissolved oxygen, containing the flavin-conjugated glucose dehydrogenase which is composed of a protein having the following amino acid sequence (a), (b), (c), (d) or (e) and glucose dehydrogenase activity, and which does not use oxygen as an electron acceptor:
(a) an amino acid sequence represented by SEQ ID NO: 3;
(b) an amino acid sequence in which 1 to 3 amino acids are deleted from, replaced in or added to the amino acid sequence represented by SEQ ID NO: 3;
(c) an amino acid sequence which has at least 80% identity with the amino acid sequence represented by SEQ ID NO: 3 and whose N-terminus is SS;
(d) an amino acid sequence which has at least 80% identity with the amino acid sequence represented by SEQ ID NO: 3, and does not contain a sequence represented by SEQ ID NO: 8 at its N-terminus;

(e) an amino acid sequence having at least 80% identity with the amino acid sequence represented by SEQ ID NO: 3.

[10] A biosensor for measuring glucose not substantially affected by dissolved oxygen, containing the flavin-conjugated glucose dehydrogenase which is composed of a protein having the following amino acid sequence (a), (b), (c), (d) or (e) and glucose dehydrogenase activity, and which does not use oxygen as an electron acceptor:

(a) an amino acid sequence represented by SEQ ID NO: 3;

(b) an amino acid sequence in which 1 to 3 amino acids are deleted from, replaced in or added to the amino acid sequence represented by SEQ ID NO: 3;

(c) an amino acid sequence which has at least 80% identity with the amino acid sequence represented by SEQ ID NO: 3 and whose N-terminus is SS;

(d) an amino acid sequence which has at least 80% identity with the amino acid sequence represented by SEQ ID NO: 3, and does not contain a sequence represented by SEQ ID NO: 8 at its N-terminus;

(e) an amino acid sequence having at least 80% identity with the amino acid sequence represented by SEQ ID NO: 3.

Effects of the Invention

The present invention provided a flavin-conjugated glucose dehydrogenase with high substrate specificity. The present invention facilitated the manufacture of the enzyme. Furthermore, using the enzyme allows measurement hardly affected by other saccharides or dissolved oxygen, and manufacturing a glucose measuring reagent composition and a biosensor which can realize measurement with high accuracy.

DESCRIPTION OF EMBODIMENTS

Figure 1:
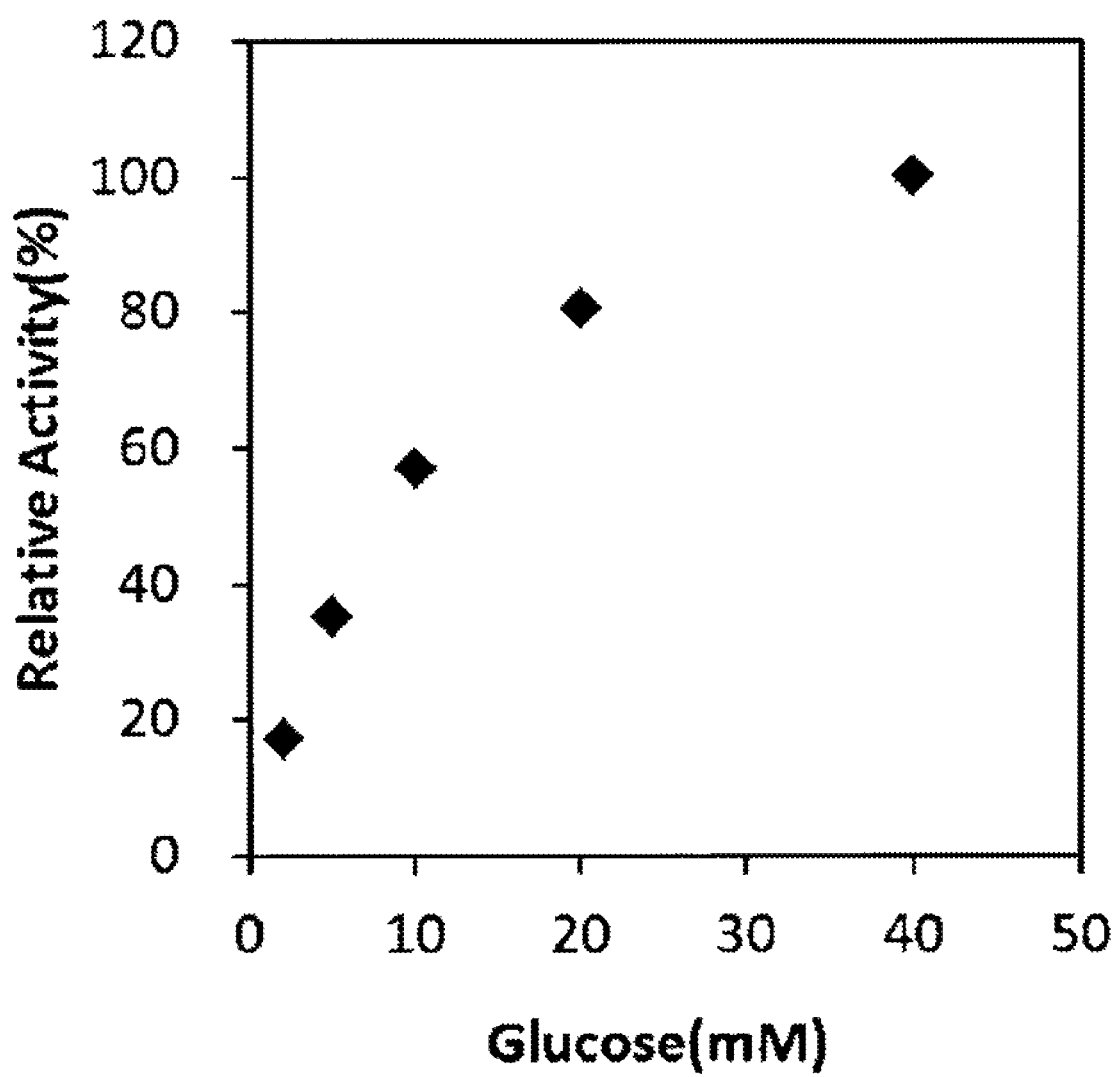
FIG. 1 illustrates a figure showing results from measurements (absorbance meter) of D-glucose by an enzyme of the present invention.

A glucose dehydrogenase according to the present invention is a protein having the following amino acid sequence (a), (b), (c), (d) or (4) and glucose dehydrogenase activity. The "protein" includes a glycoprotein.

(a) An amino acid sequence represented by SEQ ID NO: 3.

(b) An amino acid sequence in which 1, 2 or 3 amino acids are added to the amino acid sequence represented by SEQ ID NO: 3. Alternatively, an amino acid sequence in which 1 to 10, preferably 9, 8, 6, 5, 4, 3 or 2 amino acids are deleted from or replaced in the amino acid sequence represented by SEQ ID NO: 3.

(c) An amino acid sequence which has identity with the amino acid sequence represented by SEQ ID NO: 3 and whose N-terminus is SS. Preferably, the N-terminus is SSQ, SSQR, SSQRF or SSQRFD.

(d) An amino acid sequence which has identity with the amino acid sequence represented by SEQ ID NO: 3, and does not contain a sequence represented by SEQ ID NO: 8 at its N-terminus.

(e) An amino acid sequence which has identity with the amino acid sequence represented by SEQ ID NO: 3.

The identity is preferably at least 80%, 85%, 90%, 92% or 95%, more preferably 97%, 98%, 99% or 99.5%.

The enzyme is a protein preferably composed of the amino acid sequence (a), (b), (c), (d) or (e) and having glucose dehydrogenase activity.

The glucose dehydrogenase of the present invention is not particularly limited as long as it is a protein having the above-described sequences, and it may also be an enzyme obtained by culturing cells, or a synthetic enzyme obtained by synthesis. Preferably, it is a recombinant enzyme obtained by gene recombination.

The flavin-conjugated glucose dehydrogenase of the present invention has the following properties (1) to (5). The flavin may include a flavin adenine dinucleotide (FAD) and a flavin mononucleotide (FMN), and the FAD is preferable.

(1) action: the enzyme catalyzes an reaction in which glucose is oxidized in the presence of an electron acceptor.

(2) soluble.

(3) not substantially using oxygen as an electron acceptor.

(4) The substrate specificity is high. When activity on 50 mM of glucose is taken to be 100%, activity on 50 mM of maltose or D-galactose is preferably either at most 2.0%, more preferably at most 1.5%, 1.0% or 0.5%.

(5) A molecular weight of a polypeptide of the enzyme is 50 to 70 kDa. Preferably, it is 55 to 65 kDa. The molecular weight of the polypeptide of the enzyme means a molecular weight of a protein moiety measured by a SDS-polyacrylamide gel electrophoresis method after sugar chains has been removed. For the molecular weight of whole enzyme measured by the SDS-polyacrylamide gel electrophoresis method, the molecular weight is changed as the amount of the added sugar chains is changed depending on its culture condition, purification condition, etc., and in the case of a recombinant enzyme, the presence or absence of the sugar chain and the amount of the added sugar are changed and the molecular weight varies also depending on its host cell or the like. For example, the molecular weight of the whole enzyme measured by the SDS-polyacrylamide gel electrophoresis method is preferably 60 to 120 kDa, more preferably 70 to 90 kDa, and further preferably 75 to 85 kDa.

A polynucleotide according to the present invention is composed of following (i), (ii), (iii), (iv), (v) or (vi), and encodes proteins having glucose dehydrogenase activity.

(i) A polynucleotide encoding the amino acid sequence according to the above-mentioned (a), (b), (c), (d) or (e).

(ii) A polynucleotide having a base sequence represented by SEQ ID NO: 2.

(iii) A polynucleotide in which 3, 6 or 9 bases are deleted from or replaced in the base sequence represented by SEQ ID NO: 2. Alternatively, an polynucleotide having a base sequence in which 1 to 10, preferably 9, 8, 6, 5, 4, 3 or 2 bases are replaced in the base sequence represented by SEQ ID NO: 2.

(iv) A polynucleotide encoding a protein which has a base sequence having identity with the base sequence represented by SEQ ID NO: 2 and whose N-terminus is SS. Preferably, the N-terminus is SSQ, SSQR, SSQRF or SSQRFD.

(v) A polynucleotide encoding a protein which has a base sequence having identity with the base sequence represented by SEQ ID NO: 2, and does not contain a sequence represented by SEQ ID NO: 8 at its N-terminus.

(vi) A polynucleotide which has a base sequence having identity with the base sequence represented by SEQ ID NO: 1.

The identity is preferably at least 80%, 85%, 90%, 92% or 95%, more preferably 97%, 98%, 99% or 99.5%.

The identity in the present Specification shall be values of identity calculated by the homology analysis between base sequences or between amino acid sequences with GENETYX (registered trademark: GENETYX CORPORATION). Note that "GENETYX" is a Genetic Information Processing Software, and it adopts "Lipman-Pearson method" (Biochem, J. vol. 203, 527-528) as a homology analysis program.

The recombinant vector of the present invention is a cloning vector or an expression vector, and the vector can be appropriately selected. The vector includes the polynucleotide of the present invention as an insert, and moreover, a nucleic acid sequence which is heterologous to that of the insert. The polynucleotide of the present invention, as long as the expression can be occurred in a host, may be a sequence including an intron or may be a cDNA sequence. The insert may be a polynucleotide for which the codon usage is optimized according to a host cell. An expression level of the recombinant protein may be improved by replacing a termination codon by a termination codon optimal for the host. Note that, as required, an expression-contributing polynucleotide encoding proteins such as a chaperon and a lysozyme can be introduced into a vector which is the same as the polynucleotide of the present invention, and/or can be introduced into another vector so as to be held in the same host. Furthermore, the glucose dehydrogenase of the present invention can also be expressed by using a vector which can be express as a fusion protein to which various tags such as His tag, FLAG tag and GFP are added.

When the recombinant protein is expressed in the eukaryotic cell, the expression vector can be exemplified by a pUC system, pBluescriptII, a pET expression system, a pGEX expression system, a pCold expression system, etc.

When the recombinant protein is expressed in the prokaryotic cell cell, the expression vector can be exemplified by pKA1, pCDM8, pSVK3, pSVL, pBK-CMV, pBK-RSV, EBV vector, pRS, pYE82, etc.

As the host cell, e.g. prokaryotic cells such as *Escherichia coli* and *Bacillus subtilis*, eukaryotic cells such as Eumycetes (yeast, filamentous fungus (ascomycete, basidiomycete, etc.), insect cell and mammal cell, etc. can be used, and the transformant cell of the present invention can be obtained by introducing the vector of the present invention into that cell and carrying out transformation. The vector may be preserved in a transformant cell in a state like a plasmid, or may be preserved such that it is incorporated into a chromosome. Furthermore, although the host can be appropriately selected according to necessities of sugar chains and other peptide modifications, preferably a host capable of adding a sugar chain is selected to produce an enzyme having a sugar chain (glycoprotein).

A glucose dehydrogenase can be collected from a culture obtained by culturing the transformant cell of the present invention to manufacture a recombinant glucose dehydrogenase.

For culturing microorganisms used in the present invention, conventional medium for culturing microorganisms can be used. Either a synthesized medium or a natural medium may be used, as long as the medium moderately contains carbon sources, nitrogen sources, minerals and other micronutrients required by the microorganisms of use.

As the carbon sources, glucose, sucrose, dextrin, starch, glycerol, molasses, etc. can be used. As the nitrogen sources, inorganic salts such as ammonium chloride, ammonium nitrate, ammonium sulfate and ammonium phosphate, amino acids such as DL-alanine and L-glutamic acid, nitrogen-containing natural products such as peptone, meat extract, yeast extract, malt extract and corn steep liquor can be used. As the minerals, monosodium phosphate, disodium phosphate, monopotassium phosphate, dipotassium phosphate, magnesium sulfate, ferric chloride, etc. can be used.

The culturing for obtaining the glucose dehydrogenase of the present invention should be generally carried out under an aerobic condition by a method such as shake culture and aeration agitation. A culture condition suitable for production of the glucose dehydrogenase should be set in consideration of the properties of a glucose dehydrogenase-producing bacterium. For example, the culturing is carried out preferably at a culture temperature of 20° C. to 50° C., in a range of pH 4 to pH 8, and the pH may be adjusted during the culture in consideration of producibility. The culture period is preferably 2 to 10 days. By culturing with such a method, the glucose dehydrogenase can be produced and accumulated in a culture.

For the method for obtaining the glucose dehydrogenase from a culture, a conventional method for manufacturing proteins can be used. For example, first, a glucose dehydrogenase-producing bacterium is cultured, and then a culture supernatant is obtained by centrifugation. Alternatively, the cultured fungus body is obtained, the cultured microorganism is crushed by an appropriate manner, and supernatants are obtained from the crushed liquid by centrifugation or the like. Next, the glucose dehydrogenase contained in these supernatants can be purified by a conventional method for purifying proteins to obtain a purified enzyme. For example, the glucose dehydrogenase can be purified by combining purifying manipulations such as ultrafiltration, salt precipitation, solvent precipitation, heat treatment, dialysis, ion-exchange chromatography, hydrophobic chromatography, gel filtration and affinity chromatography.

The glucose dehydrogenase of the present invention can be used in a dried state. Although the drying method is not limited as long as the enzyme is not deactivated, it is preferable to obtain a lyophilized product through lyophilization. In the drying process, a buffer solution agent and a stabilizer can be added. It may be crushed and powderized so as to obtain a powdered product.

Glucose can be measured by using the glucose dehydrogenase of the present invention. The method for measuring glucose of the present invention can include a step for bringing the test sample containing glucose into contact with the glucose dehydrogenase of the present invention, so as to quantify glucose in a test sample. Although the test sample in the present invention is not particularly limited, it can be exemplified by biological samples, specifically blood, tear, saliva, urine or interstitial fluid, etc. The enzyme of the present invention is useful particularly for measuring blood sugar.

The present invention provides a manufacturing method for manufacturing a reagent composition for measuring glucose, a kit for measuring glucose, or a biosensor for measuring glucose using the glucose dehydrogenase of the present invention. Since the enzyme of the present has high substrate specificity and does not use oxygen as an electron acceptor, it is hardly affected by other saccharides and dissolved oxygen in the measured sample. Therefore, the reagent composition for measuring glucose, the kit for measuring glucose or the biosensor for measuring glucose which are hardly affected by other saccharides and dissolved oxygen can be provided, allowing the glucose measurement with high measurement accuracy.

The reagent composition for measuring glucose of the present invention may be any reagent composition as long as it contains the glucose dehydrogenase of the present invention as an enzyme. The amount of the enzyme in the composition is not particularly limited as long as the glucose in samples can be measured, but the amount of the enzyme per measurement is preferably about 0.01 to 100 U, more preferably about 0.05 to 50 U, and further preferably about 0.1 to 20 U. The composition preferably contains a buffer, and any other optional components known to those skilled in the art such as a stabilizer are preferably contained to enhance thermal stability and storage stability of the enzyme and reagent components. The composition can be exemplified by a bovine serum albumin (BSA) or egg albumin, a sugar or a sugar alcohol not interactive with the enzyme, a carboxyl group-containing compound, an alkaline earth metal compound, an ammonium salt, sulfate, proteins or the like. Furthermore, a known substance which reduces the influence from impurities affecting the measurement in the test sample may also be be contained in the measuring reagent. The kit for measuring glucose of the present invention contains the above-mentioned reagent composition, and may contain a glucose standard solution.

The biosensor of the present invention may be any sensor as long as it contains the glucose dehydrogenase of the present invention as an enzyme. For example, an electrochemical biosensor is made by comprising a substrate, a counter electrode, a working electrode, a mediator and the above-described enzyme. The mediator can be exemplified by a proteinic electronic mediator such as heme, a ferricyanide compound, a quinone compound, an osmium compound, a phenazine compound, a phenothiazine compound, etc. Moreover, a biosensor adapted to detecting ion change, coloring intensity, pH change or the like can also be constituted. Glucose measurement is possible by using this biosensor.

Furthermore, the glucose dehydrogenase of the present invention can be used for a bio battery. The bio battery of the present invention is composed of an anode electrode for oxidation reaction and a cathode electrode for reduction reaction, and optionally includes an electrolyte layer which separates between the anode and the cathode as required. An enzyme electrode containing the electron mediators and the glucose dehydrogenase is used for the anode electrode, electrons generated by oxidation of the substrate are collected on the electrode, and protons are generated. Meanwhile, an enzyme to be generally used for the cathode electrode may be used on the cathode side, for example laccase, ascorbate oxidase or bilirubin oxidase is used, and the proton generated on the anode side is reacted with oxygen to generate water. As the electrode, electrodes generally used for the bio battery, such as carbon, gold and platinum group metal can be used.

In measuring the activity of the enzyme of the present invention, the enzyme is optionally diluted to a final concentration of preferably 0.15-0.6 U/mL for use. Note that a unit of enzyme activity of the enzyme (U) means an enzyme activity for oxidizing 1 μmol of glucose in one minute. The enzyme activity of the glucose dehydrogenase of the present invention can be measured by the following method.
(Method for Measuring Glucose Dehydrogenase (GLD) Activity)

1.00 mL of 100 mM potassium phosphate buffer (pH 6.0), 1.00 mL of 1 M D-glucose solution, 0.14 mL of 3 mM 2,6-dichlorophenolindophenol (hereinafter called DCIP), and 0.20 mL of 3 mM 1-methoxy-5-methylphenazinium methylsulfate, as well as 0.61 mL of ultrapure water were mixed, kept at 37° C. for 10 minutes, and then 0.05 mL of enzyme solution was added, and the reaction was initiated. For 5 minutes from the initiation of the reaction, a decrement per one minute of the absorbance at 600 nm (ΔA600) associated with progression of the enzyme reaction was measured to calculate the enzyme activity from a straight part according to the following formula. In this measurement, for the enzyme activity, an enzyme amount for reducing 1 μmol of DCIP at 37° C., pH 6.0 per one minute was defined as 1 U.

Glucose dehydrogenase (GLD) activity (U/mL)=(−(ΔA600−ΔA600blank)×3.0×dilution ratio of enzyme)/(10.8×1.0×0.05)

Note that, in the formula, 3.0 represents a liquid volume (mL) of the reaction reagent+the enzyme solution, 10.8 represents a molar absorption coefficient of DCIP at pH 6.0, 1.0 represents an optical path length (cm) of a cell, 0.05 represents a liquid volume (mL) of the enzyme solution, and ΔA600blank represents a decrement of the absorbance at 600 nm per minute in the case that the reaction is initiated by adding a dilute solution of the enzyme instead of the enzyme solution.

Hereinafter, the present invention will be specifically explained by Examples. However, the present invention is not limited by the following Examples.

Example 1

(Obtaining the Flavin-Conjugated Glucose Dehydrogenase (GLD))

GLD-producing bacteria were searched. As a result, GLD activity has been confirmed in the culture supernatants of Glomerella fructigena NBRC5951.
(1) Culture of Fungus Bodies A liquid medium consisting of 4% (w/v) of Pinedex (Matsutani Chemical Industry Co., Ltd.), 1% (w/v) of defatted soybean (Showa Sangyo Co., Ltd.), 1% (w/v) of corn steep liquor (San-ei Sucrochemical Co., Ltd.), 0.5% (w/v) of potassium dihydrogenphosphate (NACALAI TESQUE, INC.), 0.05% (w/v) of magnesium sulfate heptahydrate (NACALAI TESQUE, INC.) and water was adjusted to have a pH of 6.0, and 10 mL of the liquid medium was introduced into a big test tube, and autoclaved at 121° C. for 20 minutes. The GLD-producing bacteria were inoculated to the cooled liquid medium, and shake-cultured at 25° C. for 72 hours, and then moist fungus body was collected by means of bleached cloth.
(2) Isolation of the Total RNA After 200 mg of the moist fungus body obtained in (1) was frozen at −80° C., 100 μg of the total RNA was extracted using ISOGENII (NIPPON GENE CO., LTD.).
(3) Preparation of a cDNA Library A cDNA library was prepared from the RNA obtained in (2) by a reverse transcription reaction, using a reverse transcriptase and an oligo dT primer with an adaptor sequence. "SMARTer RACE cDNA Amplification kit" (TAKARA BIO INC.) was used as a reaction reagent, and the reaction condition was adopted to a protocol described in an operating manual.
(4) Cloning of GLD Gene Using the cDNA library obtained in (3) as a template, PCR was carried out by using a primer pair for obtaining GLD gene. As a result, PCR products considered to be internal sequences of the GLD gene were confirmed. Note that the primer pair comprises primers designed for obtaining various GLD genes on the basis of a plurality of GLD sequences which have been already clarified by the present inventors. The PCR products was purified, and ligated to T-vector PMD20 (TAKARA BIO INC.) by using DNA Ligation Kit (TAKARA BIO INC.).

Using the obtained plasmid vector, *Escherichia coli* JM109 competent cell (TAKARA BIO INC.) was transformed by a known method. A plasmid vector was extracted/purified from the obtained transformant by using NucleoSpin Plasmid QuickPure (TAKARA BIO INC.) to determine a base sequence of an insert. On the basis of the determined base sequence, a primer for clarifying upstream and downstream sequences of each GLD gene was designed. Using these primers, the whole length of the GLD gene from an initiation codon to a termination codon, 1758 bases was clarified by a 5' RACE method and a 3' RACE method. The gene sequence was represented by SEQ ID NO: 1.

(5) Preparation of Plasmid Vector for Expression Containing GLD Gene

A plasmid vector was prepared using an amylase-based modified promoter derived from *Aspergillus oryzae* described in Known Document 1 (heterologous gene expression system of *Aspergillus*, Toshitaka MINETOKI, Chemistry and Biology, 38, 12, 831-838, 2000). First, the cDNA library obtained in (3) was used as a template to obtain a PCR product containing the GLD gene. A primer pair of the following F4570-Ori (SEQ ID NO: 4) and F4570-R-lst (SEQ ID NO: 5) was used. Then, the above-mentioned PCR product was used as a template to prepare a GfGLD gene for insertion of the veector. A primer pair of the following F4570-Ori (SEQ ID NO: 4) and F4570-R-2nd (SEQ ID NO: 6) was used.

Finally, the prepared GLD gene was bound to the downstream of the promoter to make a plasmid vector on which the gene could be expressed. The made plasmid vector for expression was introduced into *Escherichia coli* JM109 strain to transform it. The resulting transformant was cultured, and the plasmid vector was extracted from the collected fungus body using illustra plasmidPrep Midi Flow Kit (GE Healthcare). The sequence of the insert in the plasmid vector was analyzed, and then a base sequence including the GLD gene could be confirmed.

```
F4570-Ori (SEQ ID NO: 4):
5'-(CCGCAGCTCGTCAAA)ATGCTGCGCTCCATTGTCTC-3'
(in parentheses: transcription-enhancing factor)

F4570-R-1st (SEQ ID NO: 5):
5'-((GTTCATTTA)) GGCGGAAGCCTTGATGATG-3'
(in double parentheses: pSEN vector sequence)

F4570-R-2nd (SEQ ID NO: 6):
5'-((GTTACGCTTCTAGAGCATGCGTTCATTTA)) GGCGG-3'
(in double parentheses: pSEN vector sequence,
underlined: restriction enzyme site (SphI))
```

(6) Acquisition of Transformant

Using the plasmid vector extracted in (5), a recombinant mold (*Aspergillus oryzae*) which produces GLD was produced according to methods described in Known Document 2 (Biosci. Biotech. Biochem., 61 (8), 1367-1369, 1997) and Known Document 3 (genetic engineering technique for koji-mold for sake, Katsuya GOMI, journal of Brewing Society of Japan, 494-502, 2000). The obtained recombinant strain was refined in Czapek-Dox solid medium. An *Aspergillus oryzae* NS4 strain was used as a host. This strain is available as those being sold in lots at National Research Institute of Brewing, which is Incorporated Administrative Agency.

(7) Confirmation of Recombinant Mold-Derived GLD

A liquid medium consisting of 4% (w/v) of Pinedex (Matsutani Chemical Industry Co., Ltd.), 1% (w/v) of defatted soybean (Showa Sangyo Co., Ltd.), 1% (w/v) of corn steep liquor (San-ei Sucrochemical Co., Ltd.), 0.5% (w/v) of potassium dihydrogenphosphate (NACALAI TESQUE, INC.), 0.05% (w/v) of magnesium sulfate heptahydrate (NACALAI TESQUE, INC.) and water was adjusted to have a pH of 7.0, and 10 mL of the liquid medium was introduced into a big test tube (22 mm×200 mm), and autoclaved at 121° C. for 20 minutes. The transformant obtained in (6) was inoculated to the cooled liquid medium, and shake-cultured at 30° C. for 72 hours. After completing the culture, the supernatant was collected by centrifugation, GLD activity was measured by the above-mentioned method for measuring GLD activity, and as a result, the GLD activity of the present invention could be confirmed.

(8) Purification of GLD 150 mL of the liquid medium described in (7) was introduced into a Sakaguchi flask with a 500 ml capacity, and autoclaved at 121° C. for 20 minutes. The transformant obtained in (6) was inoculated to the cooled liquid medium, and shake-cultured at 30° C. for 72 hours to obtain a seed culture liquid. 3.5 L of a medium, in which 0.005% (w/v) of chloramphenicol (NACALAI TESQUE, INC.) and an anti-foaming agent were added to the same composition of the above-mentioned medium, was introduced into a jar fermentor with a 5 L capacity, and autoclaved at 121° C. for 30 minutes. 100 mL of the seed culture liquid was inoculated to the cooled liquid medium, and cultured at 30° C., 400 rpm, 1 v/v/m for 96 hours. After completing the culture, broth was filtered with a filter cloth, the collected filtrate was centrifuged to collect the supernatant, and furthermore filtrated with a membrane filter (10 μm, Advantech Co., Ltd.) to collect a crude enzyme liquid.

The collected crude enzyme liquid was purified by removing foreign proteins using Cellufine A-500(JNC CORPORATION) column and TOYOPEARL Butyl-650C (TOSOH CORPORATION) column. The purified sample was concentrated with an ultrafiltration membrane of 8,000 cutoff molecular weight, then water substitution was performed, and the obtained sample was taken to be a purified GLD. When the purified GLD was subjected to a SDS-polyacrylamide electrophoresis method, it was confirmed that it exhibited a single band.

Example 2

(Study of the Chemoenzymatic Properties of GLD of the Present Invention)

Various properties of the purified GLD obtained in Example 1 was evaluated.

(1) Measurement of Absorption Spectrum

The purified GLD of the present invention was measured for the absorption spectrum at 300-600 nm before and after addition of D-glucose using a plate reader (Spectra Max Plus 384, Molecular Devices, LLC.). As a result, the absorption maximum shown around 360-380 nm and 450-460 nm disappeared by addition of D-glucose, thus the GLD of the present invention was proved to be a flavin-conjugated protein.

0.2 mL of 1M potassium phosphate buffer (pH 7.0), 2.0 mL of 1M D-glucose, 0.2 mL of 25 mM 4-aminoantipyrine, 0.2 mL of 420 mM phenol, 0.2 mL of 1 mg/mL peroxidase and 0.2 mL of ultrapure water were mixed, and then 0.1 mL of the mixed liquid was introduced into a 96 well plate and kept at 25° C. for 5 minutes. 0.1 mL of the purified GLD obtained in Example 1 was added, and the reaction was initiated. The variation in absorbance at 500 nm associated with progression of the enzyme reaction was measured for 5 minutes from the initiation of the reaction by using the above-mentioned plate reader to examine the GOD activity. Note that, as a control, water was added instead of GLD so as to initiate the reaction. As a result, no variation in absorbance was observed for GLD as with the control.

From this result, it was confirmed that the GLD of the present invention does not have glucose oxidase activity. Therefore, it was demonstrated that since the GLD of the present invention does not oxygen as an electron acceptor, it is hardly affected by dissolved oxygen in a reaction system in quantifying D-glucose.

(3) Substrate Specificity

D-glucose, maltose or D-galactose of the final concentration of 50 mM were respectively used as a substrate to measure the activity of each GLD corresponding to each substrate according to the method for measuring GLD activity. The results are shown in Table 1.

TABLE 1

| | Relative Activity (%) |
|---|---|
| D-Glucose | 100 |
| Maltose | 0.3 |
| D-Galactose | 0.4 |

When the activity for D-glucose was taken to be 100%, the GLD of the present invention had activity of 0.3% or 0.4%, i.e., no more than 2.0%, for maltose or D-galactose.

[0054]

(4) N-Terminal Sequence

By analyzing the N-terminus of the purified GLD obtained in Example 1, it was found to be SSQRF. That is, there is a possibility that, among 1758 bases in a whole length GLD gene initiated from an initiation codon according to SEQ ID NO: 1, the 63 bases represented in SEQ ID NO: 7 are a sequence encoding a signal sequence, and the 21 amino acids represented in SEQ ID NO: 8 are signal sequences. The amino acid sequence of the mature protein obtained in Example 1 was represented by SEQ ID NO: 3, and the base sequence encoding that protein was represented by SEQ ID NO: 2.

On the other hand, when the amino acid sequence composed of 585 amino acids encoded by the whole length GLD gene 1758 bases was used to carry out BLAST search, a sequence "L2G906" having 98.6% identity was hit. L2G906 is a sequence composed of 585 amino acids derived from *Colletotrichum gloeosporioides* (strain Nara gc5) and added an annotation "glucose oxidase". Furthermore, it is said that 1-17 amino acids are signal peptides, and 18-585 amino acids are mature proteins in that sequence (uniprot.org/uniprot/L2G906). That is, a signal sequence is 17 amino acids of MLRSIVSLPLLAATALA, and an N-terminal sequence is YPAAS.

Therefore, the fact that the purified GLD obtained in Example 1 is comprised of the amino acid sequence represented by SEQ ID NO: 3, the fact that the N-terminal sequence is SSQRF, the fact that the protein comprised of amino acids represented by SEQ ID NO: 3 is not a glucose oxidase but a glucose dehydrogenase which does not use oxygen as an electron acceptor, and even the fact that the GLD of the present invention can be utilized for glucose measurement substantially not affected by dissolved oxygen, are novel technical contents over the above-mentioned L2G906, which could not be predicted at all therefrom.

(5) Molecular Weight

The molecular weight of the purified GLD obtained in Example 1 before and after cutting a sugar chain was determined by the following method. As treatment for cutting the sugar chain, 10 μL (50 mU) of endoglycosidase H (Roche) was added to the sample, and reacted with the sample at 25° C. for 16 hours. 5 μL of the GDL solutions before and after the treatment for cutting the sugar chain (each of them was prepared to be 1.0 mg/mL) and 5 μL of 0.4M sodium phosphate buffer (pH6.0) containing 1% SDS and 2% β-mercaptoethanol were mixed, and then the mixture was heat-treated at 100° C. for 3 minutes. The samples before and after the treatment for cutting the sugar chain were subjected to SDS-polyacrylamide electrophoresis using e-PAGEL (ATTO CORPORATION), and dyed with Coomassie Brilliant Blue (CBB) after the electrophoresis.

The molecular weight was determined by comparing mobility of the GLD and the molecular weight marker (ExcellBand All Blue Regular Range Protein Marker PM1500, SMOBIO Technology, Inc.). As a result, the molecular weight before cutting the sugar chain was about 83 kDa, and the molecular weight after cutting the sugar chain was about 58 kDa.

Example 3

(Drying and Powderizing of GLD)

The purified GLD obtained in Example 1 was introduced into a glass vessel, and left to stand at −80° C. for 1 hour or more so as to carry out pre-freezing. The pre-frozen GLD was introduced into a vacuum lyophilizer, and treated for approximately 16 hours. The resultant lyophilized GLD was finely crushed to collect the powdered GLD. Note that a decrease in activity was not observed after that process.

Example 4

(Measurement of Glucose by Means of Absorbance Meter)

The purified GLD obtained in Example 1 was used to measure variation in absorbance among 2, 5, 10, 20 and 40 mM D-glucose according to the above-mentioned method for measuring GLD activity. Values of relative activity in each glucose concentration were shown in FIG. 1. As a result, it was shown that D-glucose could be quantified with the GLDs of the present invention.

Example 5

(Measurement of Glucose by Means of Biosensor)

Figure 2:
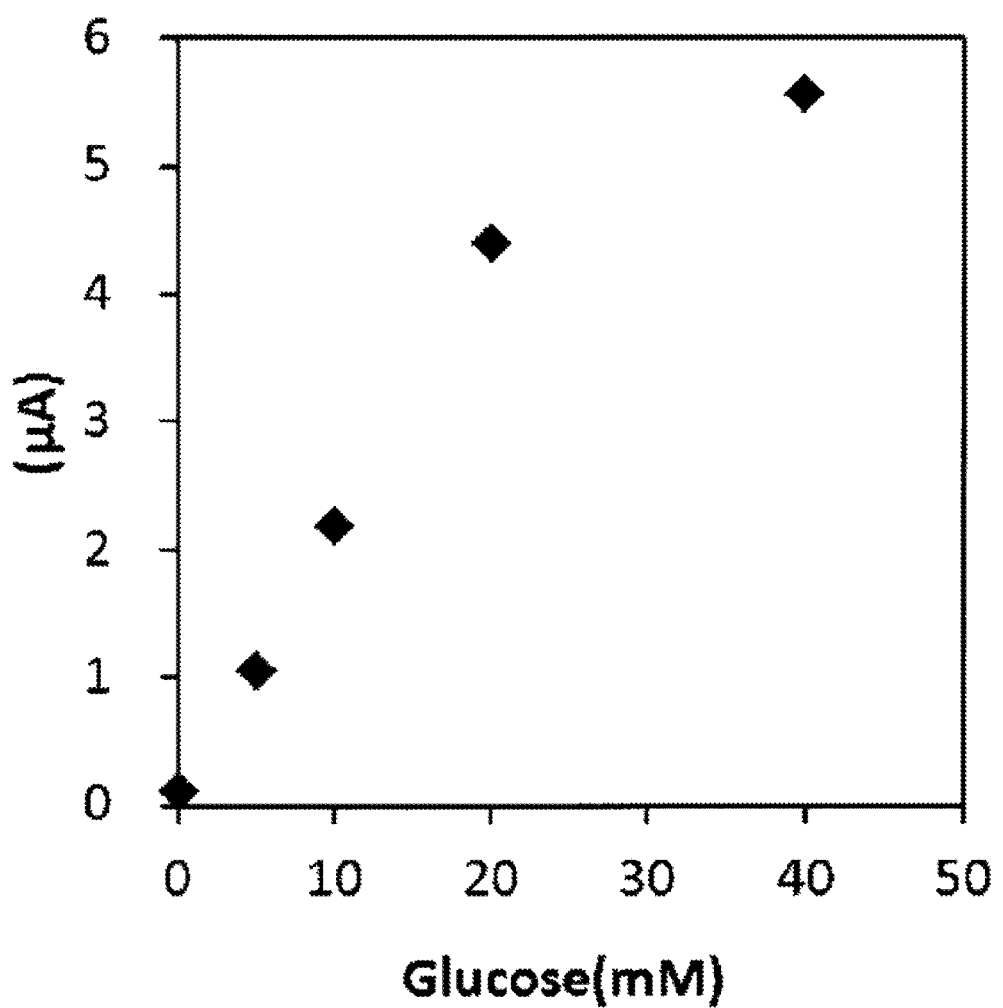
FIG. 2 illustrates a figure showing results from measurements (biosensor) of D-glucose by the enzyme of the present invention.

The GLD obtained in Example 3 was used to measure values of response current versus glucose concentrations. A reagent for measuring glucose was made so that the final concentration thereof becomes as below, 1 μL of the reagent was applied on a chip (DEP-chip, BioDevice Technology, Ltd.) and then dried. The reagent for measuring glucose: 33 mM sodium phosphate buffer (pH6.5), 10 mM mediator, 100 mM sodium chloride and 1,000 U/mL GLD. 2 μL of 0, 5, 10, 20 or 40 mM glucose solution was added to the chip, and then −0.4 to +0.4 V was applied to measure values of the response current. Current values in each glucose concentration upon application of +0.4 V were shown in FIG. 2. As a result, it was shown that D-glucose could be quantified with the GLDs of the present invention.

[Sequence Listing]
Sequence Listing (PCT-AB17001).txt

The invention claimed is:

1. A biosensor for measuring glucose not affected by dissolved oxygen, containing a flavin-conjugated glucose dehydrogenase which is composed of a protein having the following amino acid sequence (a), (b), (c), (d) or (e) and glucose dehydrogenase activity, and which does not use oxygen as an electron acceptor:
  (a) the amino acid sequence of SEQ ID NO: 3;
  (b) an amino acid sequence in which 1 to 3 amino acids are deleted from, replaced in or added to the amino acid sequence of SEQ ID NO: 3;
  (c) an amino acid sequence which has at least 92% identity with the amino acid sequence of SEQ ID NO: 3 and whose N-terminus is SSQRF;
  (d) an amino acid sequence which has at least 92% identity with the amino acid sequence of SEQ ID NO: 3, and does not contain a sequence of SEQ ID NO: 8 at its N-terminus;
  (e) an amino acid sequence having at least 92% identity with the amino acid sequence of SEQ ID NO: 3.

2. The biosensor for measuring glucose not affected by dissolved oxygen of claim 1, further comprising a substrate, a counter electrode, a working electrode, and a mediator.

3. The biosensor for measuring glucose of claim 1, wherein the amino acid sequence of (a)-(e) has at least 95% identity with the amino acid sequence of SEQ ID NO: 3.

4. The biosensor for measuring glucose of claim 3, further comprising a substrate, a counter electrode, a working electrode, and a mediator.

5. The biosensor for measuring glucose of claim 1, wherein the amino acid sequence of (a)-(e) has at least 99% identity with the amino acid sequence of SEQ ID NO: 3.

6. The biosensor for measuring glucose of claim 5, further comprising a substrate, a counter electrode, a working electrode, and a mediator.

7. A method for measuring glucose not affected by dissolved oxygen, using the biosensor of claim 1.

* * * * *

SEQUENCE LISTING

<160> NUMBER OF SEQ ID NOS: 8

<210> SEQ ID NO 1
<211> LENGTH: 1758
<212> TYPE: DNA
<213> ORGANISM: Glomerella fructibena NBRC5951
<220> FEATURE:
<221> NAME/KEY: DNA
<222> LOCATION: (1)..(1758)

<400> SEQUENCE: 1

```
atgctgcgct ccattgtctc cctcccgctt cttgcggcca ccgcgctcgc ctatcccgct    60
gcatcttcgc agcgcttcga ctatgtcatt atcggtggtg gtaccagcgg tctcgtcgtt   120
gccaaccgtc tttccgagtt gaacaatgtc accgtcgctg tcattgaggc cggtgactct   180
gtctacgaca cgacaacgt gaccagcccc tctggctacg gactggcctt tggtaccgac   240
atcgactacg cctatcagac tactgcccag aagtatggcg gcaacaagac tcagaccctc   300
cgtgccggca aggctctcgg cggtaccagc accatcaacg gcatggctta cacccgtgct   360
caggacgttc agatcgacat ctgggagcgt cttggcaacg acggctggaa ctggaacaac   420
cttctcaagt actacaagaa gtccgagact ctccagcccc ccaccactgt ccaggttgac   480
gatggcgtca cctacatccc tgagcagcac ggtacctctg gtcctctcaa ggtcggctgg   540
aagtccggcg gtgtcgagaa gtccttcgtc gacgtcttga accagaccta caatgccgtt   600
ggcgtccctg ccctgaagga cattgctggt ggagacatgg tcggctggaa catctacccc   660
gccaccctgg acactgctct tcaggttcgc gatgatgctg cccgcgcgta ctacttcccc   720
taccagaacc gcaccaactt ccgcgtcttc ttgaacaccg aggctcagaa actcgtctgg   780
gctgagggag ctgaggccac cgcctccgga gttctcgtca aggacaagac cggtgctacc   840
cacaccgtct atgccaacaa ggaggtcatt ctctctgctg gctctctcag atctcctctc   900
ctcctggagc agtccggtgt aggaaacccc gagatcctga aggccgccgg catccagact   960
aagctcaacc tccccaccgt cggtgagaac ctccaggacc agatgaacaa cggcctcgcc  1020
cagaccagct ccaagaactt caccggtgtc accaccttcg ttgcctaccc caacgtcgac  1080
gacgtcttcg caaaccagac cgcttccctc gctgccaaca tcaagaccca gctctcccag  1140
tgggccgacc aggtctccga gtacaccaaa ggcgtcgtca ccaaggagca gctcaacaag  1200
ttcttcgaca tccagtacga cctcatcttc accgacaagg tcccctcgc tgagatcctg  1260
atcaccctg ccggttcttc cttctccacc gagtactggg ccctcctgcc cttcgctcgc  1320
ggcaacatcc atgtcaccgg cgccaactcc tctgctgcca agatcaaccc caactacttc  1380
atgatggact gggacatgac cgagcagatt ggcaccgcca agttcatccg tcagctgtac  1440
aagactgccc tctgagcca gtacttcgcc agcgagacca agcctggttt ggccaccatc  1500
gccgaggacg cctctgacga tgtttggtcc aagtggatcc ttgagaacta ccgctccaac  1560
ttccacccog tcggcaccac cgccatgatg tcaaaggagc tgggcggtgt tgtcgatgcc  1620
aacctcaagg tctacggcac cagcaacgtc cgcgtcgtcg atgccggtgt cctgcctttc  1680
caggtttgcg ccaccttgt gtccactctc tacgccattg ccgagaaggc ttcggacatc  1740
atcaaggctt ccgcctag                                                1758
```

<210> SEQ ID NO 2
<211> LENGTH: 1695

<212> TYPE: DNA
<213> ORGANISM: Glomerella fructigena NBRC5951
<220> FEATURE:
<221> NAME/KEY: CDS
<222> LOCATION: (1)..(1695)

<400> SEQUENCE: 2

| | | | | | | | | | | | | | | | | |
|---|---|---|---|---|---|---|---|---|---|---|---|---|---|---|---|---|
| tct | tcg | cag | cgc | ttc | gac | tat | gtc | att | atc | ggt | ggt | ggt | acc | agc | ggt | 48 |
| Ser | Ser | Gln | Arg | Phe | Asp | Tyr | Val | Ile | Ile | Gly | Gly | Gly | Thr | Ser | Gly | |
| 1 | | | | 5 | | | | | 10 | | | | | 15 | | |
| ctc | gtc | gtt | gcc | aac | cgt | ctt | tcc | gag | ttg | aac | aat | gtc | acc | gtc | gct | 96 |
| Leu | Val | Val | Ala | Asn | Arg | Leu | Ser | Glu | Leu | Asn | Asn | Val | Thr | Val | Ala | |
| | | | 20 | | | | | 25 | | | | | 30 | | | |
| gtc | att | gag | gcc | ggt | gac | tct | gtc | tac | gac | aac | gac | aac | gtg | acc | agc | 144 |
| Val | Ile | Glu | Ala | Gly | Asp | Ser | Val | Tyr | Asp | Asn | Asp | Asn | Val | Thr | Ser | |
| | | 35 | | | | | 40 | | | | | 45 | | | | |
| ccc | tct | ggc | tac | gga | ctg | gcc | ttt | ggt | acc | gac | atc | gac | tac | gcc | tat | 192 |
| Pro | Ser | Gly | Tyr | Gly | Leu | Ala | Phe | Gly | Thr | Asp | Ile | Asp | Tyr | Ala | Tyr | |
| | 50 | | | | | 55 | | | | | 60 | | | | | |
| cag | act | act | gcc | cag | aag | tat | ggc | ggc | aac | aag | act | cag | acc | ctc | cgt | 240 |
| Gln | Thr | Thr | Ala | Gln | Lys | Tyr | Gly | Gly | Asn | Lys | Thr | Gln | Thr | Leu | Arg | |
| 65 | | | | | 70 | | | | | 75 | | | | | 80 | |
| gcc | ggc | aag | gct | ctc | ggc | ggt | acc | agc | acc | atc | aac | ggc | atg | gct | tac | 288 |
| Ala | Gly | Lys | Ala | Leu | Gly | Gly | Thr | Ser | Thr | Ile | Asn | Gly | Met | Ala | Tyr | |
| | | | | 85 | | | | | 90 | | | | | 95 | | |
| acc | cgt | gct | cag | gac | gtt | cag | atc | gac | atc | tgg | gag | cgt | ctt | ggc | aac | 336 |
| Thr | Arg | Ala | Gln | Asp | Val | Gln | Ile | Asp | Ile | Trp | Glu | Arg | Leu | Gly | Asn | |
| | | | 100 | | | | | 105 | | | | | 110 | | | |
| gac | ggc | tgg | aac | tgg | aac | aac | ctt | ctc | aag | tac | tac | aag | aag | tcc | gag | 384 |
| Asp | Gly | Trp | Asn | Trp | Asn | Asn | Leu | Leu | Lys | Tyr | Tyr | Lys | Lys | Ser | Glu | |
| | | 115 | | | | | 120 | | | | | 125 | | | | |
| act | ctc | cag | ccc | ccc | acc | act | gtc | cag | gtt | gac | gat | ggc | gtc | acc | tac | 432 |
| Thr | Leu | Gln | Pro | Pro | Thr | Thr | Val | Gln | Val | Asp | Asp | Gly | Val | Thr | Tyr | |
| | 130 | | | | | 135 | | | | | 140 | | | | | |
| atc | cct | gag | cag | cac | ggt | acc | tct | ggt | cct | ctc | aag | gtc | ggc | tgg | aag | 480 |
| Ile | Pro | Glu | Gln | His | Gly | Thr | Ser | Gly | Pro | Leu | Lys | Val | Gly | Trp | Lys | |
| 145 | | | | | 150 | | | | | 155 | | | | | 160 | |
| tcc | ggc | ggt | gtc | gag | aag | tcc | ttc | gtc | gac | gtc | ttg | aac | cag | acc | tac | 528 |
| Ser | Gly | Gly | Val | Glu | Lys | Ser | Phe | Val | Asp | Val | Leu | Asn | Gln | Thr | Tyr | |
| | | | | 165 | | | | | 170 | | | | | 175 | | |
| aat | gcc | gtt | ggc | gtc | cct | gcc | ctg | aag | gac | att | gct | ggt | gga | gac | atg | 576 |
| Asn | Ala | Val | Gly | Val | Pro | Ala | Leu | Lys | Asp | Ile | Ala | Gly | Gly | Asp | Met | |
| | | | 180 | | | | | 185 | | | | | 190 | | | |
| gtc | ggc | tgg | aac | atc | tac | ccc | gcc | acc | ctg | gac | act | gct | ctt | cag | gtt | 624 |
| Val | Gly | Trp | Asn | Ile | Tyr | Pro | Ala | Thr | Leu | Asp | Thr | Ala | Leu | Gln | Val | |
| | | 195 | | | | | 200 | | | | | 205 | | | | |
| cgc | gat | gat | gct | gcc | cgc | gcg | tac | tac | ttc | ccc | tac | cag | aac | cgc | acc | 672 |
| Arg | Asp | Asp | Ala | Ala | Arg | Ala | Tyr | Tyr | Phe | Pro | Tyr | Gln | Asn | Arg | Thr | |
| | 210 | | | | | 215 | | | | | 220 | | | | | |
| aac | ttc | cgc | gtc | ttc | ttg | aac | acc | gag | gct | cag | aaa | ctc | gtc | tgg | gct | 720 |
| Asn | Phe | Arg | Val | Phe | Leu | Asn | Thr | Glu | Ala | Gln | Lys | Leu | Val | Trp | Ala | |
| 225 | | | | | 230 | | | | | 235 | | | | | 240 | |
| gag | gga | gct | gag | gcc | acc | gcc | tcc | gga | gtt | ctc | gtc | aag | gac | aag | acc | 768 |
| Glu | Gly | Ala | Glu | Ala | Thr | Ala | Ser | Gly | Val | Leu | Val | Lys | Asp | Lys | Thr | |
| | | | | 245 | | | | | 250 | | | | | 255 | | |
| ggt | gct | acc | cac | acc | gtc | tat | gcc | aac | aag | gag | gtc | att | ctc | tct | gct | 816 |
| Gly | Ala | Thr | His | Thr | Val | Tyr | Ala | Asn | Lys | Glu | Val | Ile | Leu | Ser | Ala | |
| | | | 260 | | | | | 265 | | | | | 270 | | | |
| ggc | tct | ctc | aga | tct | cct | ctc | ctc | ctg | gag | cag | tcc | ggt | gta | gga | aac | 864 |
| Gly | Ser | Leu | Arg | Ser | Pro | Leu | Leu | Leu | Glu | Gln | Ser | Gly | Val | Gly | Asn | |
| | | 275 | | | | | 280 | | | | | 285 | | | | |

```
ccc gag atc ctg aag gcc gcc ggc atc cag act aag ctc aac ctc ccc    912
Pro Glu Ile Leu Lys Ala Ala Gly Ile Gln Thr Lys Leu Asn Leu Pro
    290                 295                 300 acc gtc ggt gag aac ctc cag gac cag atg aac aac ggc ctc gcc cag    960
Thr Val Gly Glu Asn Leu Gln Asp Gln Met Asn Asn Gly Leu Ala Gln
305                 310                 315                 320 acc agc tcc aag aac ttc acc ggt gtc acc acc ttc gtt gcc tac ccc   1008
Thr Ser Ser Lys Asn Phe Thr Gly Val Thr Thr Phe Val Ala Tyr Pro
                325                 330                 335 aac gtc gac gac gtc ttc gca aac cag acc gct tcc ctc gct gcc aac   1056
Asn Val Asp Asp Val Phe Ala Asn Gln Thr Ala Ser Leu Ala Ala Asn
            340                 345                 350 atc aag acc cag ctc tcc cag tgg gcc gac cag gtc tcc gag tac acc   1104
Ile Lys Thr Gln Leu Ser Gln Trp Ala Asp Gln Val Ser Glu Tyr Thr
        355                 360                 365 aaa ggc gtc gtc acc aag gag cag ctc aac aag ttc ttc gac atc cag   1152
Lys Gly Val Val Thr Lys Glu Gln Leu Asn Lys Phe Phe Asp Ile Gln
370                 375                 380 tac gac ctc atc ttc acc gac aag gtc ccc ctc gct gag atc ctg atc   1200
Tyr Asp Leu Ile Phe Thr Asp Lys Val Pro Leu Ala Glu Ile Leu Ile
385                 390                 395                 400 acc cct gcc ggt tct tcc ttc tcc acc gag tac tgg gcc ctc ctg ccc   1248
Thr Pro Ala Gly Ser Ser Phe Ser Thr Glu Tyr Trp Ala Leu Leu Pro
                405                 410                 415 ttc gct cgc ggc aac atc cat gtc acc ggc gcc aac tcc tct gct gcc   1296
Phe Ala Arg Gly Asn Ile His Val Thr Gly Ala Asn Ser Ser Ala Ala
            420                 425                 430 aag atc aac ccc aac tac ttc atg atg gac tgg gac atg acc gag cag   1344
Lys Ile Asn Pro Asn Tyr Phe Met Met Asp Trp Asp Met Thr Glu Gln
        435                 440                 445 att ggc acc gcc aag ttc atc cgt cag ctg tac aag act gcc cct ctg   1392
Ile Gly Thr Ala Lys Phe Ile Arg Gln Leu Tyr Lys Thr Ala Pro Leu
450                 455                 460 agc cag tac ttc gcc agc gag acc aag cct ggt ttg gcc acc atc gcc   1440
Ser Gln Tyr Phe Ala Ser Glu Thr Lys Pro Gly Leu Ala Thr Ile Ala
465                 470                 475                 480 gag gac gcc tct gac gat gtt tgg tcc aag tgg atc ctt gag aac tac   1488
Glu Asp Ala Ser Asp Asp Val Trp Ser Lys Trp Ile Leu Glu Asn Tyr
                485                 490                 495 cgc tcc aac ttc cac ccc gtc ggc acc acc gcc atg atg tca aag gag   1536
Arg Ser Asn Phe His Pro Val Gly Thr Thr Ala Met Met Ser Lys Glu
            500                 505                 510 ctg ggc ggt gtt gtc gat gcc aac ctc aag gtc tac ggc acc agc aac   1584
Leu Gly Gly Val Val Asp Ala Asn Leu Lys Val Tyr Gly Thr Ser Asn
        515                 520                 525 gtc cgc gtc gtc gat gcc ggt gtc ctg cct ttc cag gtt tgc ggc cac   1632
Val Arg Val Val Asp Ala Gly Val Leu Pro Phe Gln Val Cys Gly His
530                 535                 540 ctt gtg tcc act ctc tac gcc att gcc gag aag gct tcg gac atc atc   1680
Leu Val Ser Thr Leu Tyr Ala Ile Ala Glu Lys Ala Ser Asp Ile Ile
545                 550                 555                 560 aag gct tcc gcc tag                                                1695
Lys Ala Ser Ala <210> SEQ ID NO 3
<211> LENGTH: 564
<212> TYPE: PRT
<213> ORGANISM: Glomerella fructigena NBRC5951

<400> SEQUENCE: 3
```

```
Ser Ser Gln Arg Phe Asp Tyr Val Ile Ile Gly Gly Thr Ser Gly
1               5                   10                  15

Leu Val Val Ala Asn Arg Leu Ser Glu Leu Asn Val Thr Val Ala
                20                  25                  30

Val Ile Glu Ala Gly Asp Ser Val Tyr Asp Asn Asp Asn Val Thr Ser
        35                  40                  45

Pro Ser Gly Tyr Gly Leu Ala Phe Gly Thr Asp Ile Asp Tyr Ala Tyr
    50                  55                  60

Gln Thr Thr Ala Gln Lys Tyr Gly Gly Asn Lys Thr Gln Thr Leu Arg
65                  70                  75                  80

Ala Gly Lys Ala Leu Gly Gly Thr Ser Thr Ile Asn Gly Met Ala Tyr
                85                  90                  95

Thr Arg Ala Gln Asp Val Gln Ile Asp Ile Trp Glu Arg Leu Gly Asn
            100                 105                 110

Asp Gly Trp Asn Trp Asn Asn Leu Leu Lys Tyr Tyr Lys Lys Ser Glu
            115                 120                 125

Thr Leu Gln Pro Pro Thr Thr Val Gln Val Asp Asp Gly Val Thr Tyr
        130                 135                 140

Ile Pro Glu Gln His Gly Thr Ser Gly Pro Leu Lys Val Gly Trp Lys
145                 150                 155                 160

Ser Gly Gly Val Glu Lys Ser Phe Val Asp Val Leu Asn Gln Thr Tyr
                165                 170                 175

Asn Ala Val Gly Val Pro Ala Leu Lys Asp Ile Ala Gly Gly Asp Met
                180                 185                 190

Val Gly Trp Asn Ile Tyr Pro Ala Thr Leu Asp Thr Ala Leu Gln Val
            195                 200                 205

Arg Asp Asp Ala Ala Arg Ala Tyr Tyr Phe Pro Tyr Gln Asn Arg Thr
210                 215                 220

Asn Phe Arg Val Phe Leu Asn Thr Glu Ala Gln Lys Leu Val Trp Ala
225                 230                 235                 240

Glu Gly Ala Glu Ala Thr Ala Ser Gly Val Leu Val Lys Asp Lys Thr
                245                 250                 255

Gly Ala Thr His Thr Val Tyr Ala Asn Lys Glu Val Ile Leu Ser Ala
            260                 265                 270

Gly Ser Leu Arg Ser Pro Leu Leu Leu Glu Gln Ser Gly Val Gly Asn
            275                 280                 285

Pro Glu Ile Leu Lys Ala Ala Gly Ile Gln Thr Lys Leu Asn Leu Pro
        290                 295                 300

Thr Val Gly Glu Asn Leu Gln Asp Gln Met Asn Asn Gly Leu Ala Gln
305                 310                 315                 320

Thr Ser Ser Lys Asn Phe Thr Gly Val Thr Thr Phe Val Ala Tyr Pro
                325                 330                 335

Asn Val Asp Asp Val Phe Ala Asn Gln Thr Ala Ser Leu Ala Ala Asn
                340                 345                 350

Ile Lys Thr Gln Leu Ser Gln Trp Ala Asp Gln Val Ser Glu Tyr Thr
            355                 360                 365

Lys Gly Val Val Thr Lys Glu Gln Leu Asn Lys Phe Phe Asp Ile Gln
370                 375                 380

Tyr Asp Leu Ile Phe Thr Asp Lys Val Pro Leu Ala Glu Ile Leu Ile
385                 390                 395                 400

Thr Pro Ala Gly Ser Ser Phe Ser Thr Glu Tyr Trp Ala Leu Leu Pro
                405                 410                 415
```

```
Phe Ala Arg Gly Asn Ile His Val Thr Gly Ala Asn Ser Ser Ala Ala
                420                 425                 430

Lys Ile Asn Pro Asn Tyr Phe Met Met Asp Trp Asp Met Thr Glu Gln
            435                 440                 445

Ile Gly Thr Ala Lys Phe Ile Arg Gln Leu Tyr Lys Thr Ala Pro Leu
        450                 455                 460

Ser Gln Tyr Phe Ala Ser Glu Thr Lys Pro Gly Leu Ala Thr Ile Ala
465                 470                 475                 480

Glu Asp Ala Ser Asp Val Trp Ser Lys Trp Ile Leu Glu Asn Tyr
                485                 490                 495

Arg Ser Asn Phe His Pro Val Gly Thr Thr Ala Met Met Ser Lys Glu
                500                 505                 510

Leu Gly Gly Val Val Asp Ala Asn Leu Lys Val Tyr Gly Thr Ser Asn
            515                 520                 525

Val Arg Val Val Asp Ala Gly Val Leu Pro Phe Gln Val Cys Gly His
        530                 535                 540

Leu Val Ser Thr Leu Tyr Ala Ile Ala Glu Lys Ala Ser Asp Ile Ile
545                 550                 555                 560

Lys Ala Ser Ala

<210> SEQ ID NO 4
<211> LENGTH: 35
<212> TYPE: DNA
<213> ORGANISM: Artificial Sequence
<220> FEATURE:
<223> OTHER INFORMATION: primer:F4570-Ori
<220> FEATURE:
<221> NAME/KEY: DNA
<222> LOCATION: (1)..(35)

<400> SEQUENCE: 4
ccgcagctcg tcaaaatgct gcgctccatt gtctc                              35

<210> SEQ ID NO 5
<211> LENGTH: 28
<212> TYPE: DNA
<213> ORGANISM: Artificial Sequence
<220> FEATURE:
<223> OTHER INFORMATION: primer:F4570-R-1st
<220> FEATURE:
<221> NAME/KEY: DNA
<222> LOCATION: (1)..(28)

<400> SEQUENCE: 5
gttcatttag gcggaagcct tgatgatg                                      28

<210> SEQ ID NO 6
<211> LENGTH: 34
<212> TYPE: DNA
<213> ORGANISM: Artificial Sequence
<220> FEATURE:
<223> OTHER INFORMATION: primer:F4570-R-2nd
<220> FEATURE:
<221> NAME/KEY: DNA
<222> LOCATION: (1)..(34)

<400> SEQUENCE: 6
gttacgcttc tagagcatgc gttcatttag gcgg                               34

<210> SEQ ID NO 7
<211> LENGTH: 63
<212> TYPE: DNA
<213> ORGANISM: Glomerella fructigena NBRC5951
```

```
<400> SEQUENCE: 7
atgacgctct ttcgccagtc caagtcctgg cccgggctcg cctccgcagc cctgctcgcc      60
gtg                                                                   63

<210> SEQ ID NO 8
<211> LENGTH: 21
<212> TYPE: PRT
<213> ORGANISM: Glomerella fructigena NBRC5951

<400> SEQUENCE: 8

Met Leu Arg Ser Ile Val Ser Leu Pro Leu Leu Ala Ala Thr Ala Leu
1               5                   10                  15

Ala Tyr Pro Ala Ala
            20
```